(12) United States Patent
Babson et al.

(10) Patent No.: US 12,733,794 B2
(45) Date of Patent: Sep. 15, 2026

(54) VISUALLY LINEAR AND DISCRETE DIMMING FOR OPHTHALMOSCOPES AND OTOSCOPES AND OTHER MEDICAL EXAMINATION OR DIAGNOSTIC INSTRUMENTS

(71) Applicant: Welch Allyn, Inc., Skaneateles Falls, NY (US)

(72) Inventors: David Matthew Babson, Warners, NY (US); Kenneth V. Coon, III, Jordan, NY (US); David Gregory Perkins, Tully, NY (US); James Paul Knoop, Syracuse, NY (US); James Stuart Ledwith, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1185 days.

(21) Appl. No.: 17/724,323

(22) Filed: Apr. 19, 2022

(65) Prior Publication Data

US 2022/0330793 A1 Oct. 20, 2022

Related U.S. Application Data

(60) Provisional application No. 63/176,853, filed on Apr. 19, 2021.

(51) Int. Cl.
*A61B 1/00* (2006.01)
*A61B 1/06* (2006.01)
(Continued)

(52) U.S. Cl.
CPC ........ *A61B 1/00105* (2013.01); *A61B 1/0684* (2013.01); *A61B 1/227* (2013.01); *A61B 3/0008* (2013.01); *A61B 3/1208* (2013.01)

(58) Field of Classification Search
CPC ... A61B 1/00105; A61B 1/0684; A61B 1/227; A61B 3/0008; A61B 3/1208
See application file for complete search history.

(56) References Cited

U.S. PATENT DOCUMENTS 5,239,984 A 8/1993 Cane et al.
8,823,287 B2 9/2014 Munari et al.
(Continued)

FOREIGN PATENT DOCUMENTS

CN 103298391 A 9/2013
CN 203898253 U 10/2014
(Continued)

OTHER PUBLICATIONS

PCT Search Report and Written Opinion mailed Jul. 4, 2022 for PCT Application No. PCT/US2022/025369, 11 pages.
(Continued)

*Primary Examiner* — Nicholas J Plionis
(74) *Attorney, Agent, or Firm* — Lee & Hayes, P.C.

(57) ABSTRACT

Disclosed are medical examination or diagnostic instruments and methods of operating such instruments. The method can include coupling an instrument head to a handle to form a medical examination or diagnostic instrument; detecting by the instrument head, a characteristic of the handle; and based at least in part on detecting the characteristic of the handle, determining, by the instrument head, a handle type associated with the handle, or detecting by the handle, a characteristic of the instrument head, and based at least in part on detecting the characteristic of the instrument head, an instrument head type associated with the instrument head. In some implementations, the emission of light can be controlled to be approximately linear in relation to a user input signal, as perceived by a user.

19 Claims, 12 Drawing Sheets

(51) Int. Cl.

| | |
|---|---|
| ***A61B 1/227*** | (2006.01) |
| ***A61B 3/00*** | (2006.01) |
| ***A61B 3/12*** | (2006.01) |

(56) References Cited

U.S. PATENT DOCUMENTS

| | | | | |
|---|---|---|---|---|
| 8,890,489 | B2 | 11/2014 | Wood | |
| 9,198,560 | B2 | 12/2015 | Davis et al. | |
| 9,393,078 | B2 | 7/2016 | Shibahara et al. | |
| 9,859,909 | B1 | 1/2018 | Cowan | |
| 10,143,050 | B2 | 11/2018 | Nieuwlands | |
| 10,278,681 | B2 | 5/2019 | Wood et al. | |
| 2003/0095406 | A1 | 5/2003 | Lebens et al. | |
| 2004/0183482 | A1 | 9/2004 | Roberts et al. | |
| 2016/0249805 | A1 | 9/2016 | Salvati | |
| 2016/0374546 | A1* | 12/2016 | Berbee | A61B 1/05 600/109 |
| 2019/0216307 | A1* | 7/2019 | Coon | A61B 1/00124 |
| 2019/0265490 | A1* | 8/2019 | Duckett, III | A61B 1/0019 |

FOREIGN PATENT DOCUMENTS

| | | | |
|---|---|---|---|
| CN | 107692960 | A | 2/2018 |
| CN | 111629644 | A | 9/2020 |
| JP | 2019117719 | A | 7/2019 |
| WO | WO2014105649 | A1 | 7/2014 |
| WO | WO2016193984 | A1 | 12/2016 |
| WO | WO2019143668 | A1 | 7/2019 |
| WO | WO2020233652 | A1 | 11/2020 |

OTHER PUBLICATIONS

Office Action for Chinese Application No. 202280001767.9, dated Jun. 19, 2025, 18 pages.

* cited by examiner 40
18
48
46
27
10
30
31
58

14
26
26
33

1020
Incan-
descent
1005
1014
Mechanical
Interface
Electrical
Interface
1004
1013
1011
Mechanical
Interface
Ring
Pin
1002
1012
Power
Rheostat
1001
1003

VISUALLY LINEAR AND DISCRETE DIMMING FOR OPHTHALMOSCOPES AND OTOSCOPES AND OTHER MEDICAL EXAMINATION OR DIAGNOSTIC INSTRUMENTS

CROSS-REFERENCE TO RELATED APPLICATIONS

This application claims the benefit of and priority to U.S. Provisional Patent Appl. No. 63/176,853 filed on Apr. 19, 2021, which is incorporated by reference in its entirety as if fully set forth herein.

TECHNICAL FIELD

This disclosure generally relates to the field of illumination, and more particularly, to a replacement light assembly for hand-held and other medical examination or diagnostic instruments, such as those used in physicians' offices, healthcare facilities, or other medical environments.

BACKGROUND

Visual observation is a common technique for healthcare providers to determine a patient's health status. Many medical examination or diagnostic instruments exist to assist healthcare providers with visual observations of patients. Such medical examination or diagnostics instruments can include a range of instruments, such as otoscopes, ophthalmoscope, dermatoscopes and others that include a light source including those with adjustable light intensity. For example, an otoscope assists healthcare providers with viewing inside of a patient's ear, such as during regular health check-ups and/or to investigate ear symptoms. An ophthalmoscope assists healthcare providers with viewing inside of the fundus of a patient's eye, such as part of an eye exam and/or a routine physical exam. A dermatoscope assists healthcare providers with viewing skin lesions without the interference of skin surface reflections, which is useful in distinguishing between benign and malignant lesions on a patient's skin. These are but a few examples of tools that may assist a healthcare provider with visual observations of a patient.

In particular, ophthalmoscopes provide a very useful view of the patient's retina, but light levels can be uncomfortable for patients. Otoscopes light levels can result in glare and difficulty interpreting the view. In general for these medical examination or diagnostic instruments and other light sources used in medical diagnosis, the dilation of the pupil in the human eye results in a non-linear perceived vs absolute light relationship as described by the formula:

$$\text{Perceived Light (\%)} = 100 * \sqrt{\frac{\text{Measured Light (\%)}}{100}} \quad \text{(Equation 1)}$$

where,

Perceived Light is as a percent of maximum, and

Measured Light is as a percent of maximum.

Thus, one percent actual light will be perceived as approximately ten percent by a clinician or patient and attempting to adjust an instrument at low light levels becomes difficult. When adjusting the light at the lowest level, users can accidentally turn the handle off, which on many handles locks the handle in an off position.

Examples of the present disclosure are directed toward overcoming the deficiencies described above.

SUMMARY

An example method includes coupling an instrument head to a handle to form a medical examination or diagnostic instrument; detecting by the instrument head, a characteristic of the handle; and based at least in part on detecting the characteristic of the handle, determining, by the instrument head, a handle type associated with the handle, or detecting by the handle, a characteristic of the instrument head, and based at least in part on detecting the characteristic of the instrument head, an instrument head type associated with the instrument head. Some examples of such a method are also configured for control of the light emitted from a light source in the instrument head, for example where the control of the light source is configured to an approximately linear relationship between a user input signal and an amount of light emitted by the light source as perceived by a person, such as the user. The user input signal can be the signal generated by the user operating a control of the medical examination or diagnostic instrument, such as by turning a dial, sliding of a rheostat, or operating of a button.

An example of a medical examination or diagnostic instrument can include an instrument head; a handle; one or more processors; and one or more non-transitory computer-readable media storing computer-executable instructions that, when executed by the one or more processors, cause the one or more processors to perform actions comprising: detecting, by the instrument head, a characteristic of the handle; and based at least in part on detecting the characteristic of the handle, determining, by the instrument head, a handle type associated with the handle. Some examples of such a medical examination or diagnostic instrument are also configured for control of the light emitted from a light source in the instrument head, for example where the control of the light source is configured to an approximately linear relationship between a user input signal and an amount of light emitted by the light source as perceived by a person, such as the user. The user input signal can be the signal generated by the user operating a control of the medical examination or diagnostic instrument, such as by turning a dial, sliding of a rheostat, or operating of a button on the handle or instrument head of the medical examination or diagnostic instrument.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

DESCRIPTION OF EXAMPLE EMBODIMENTS

Figure 1:
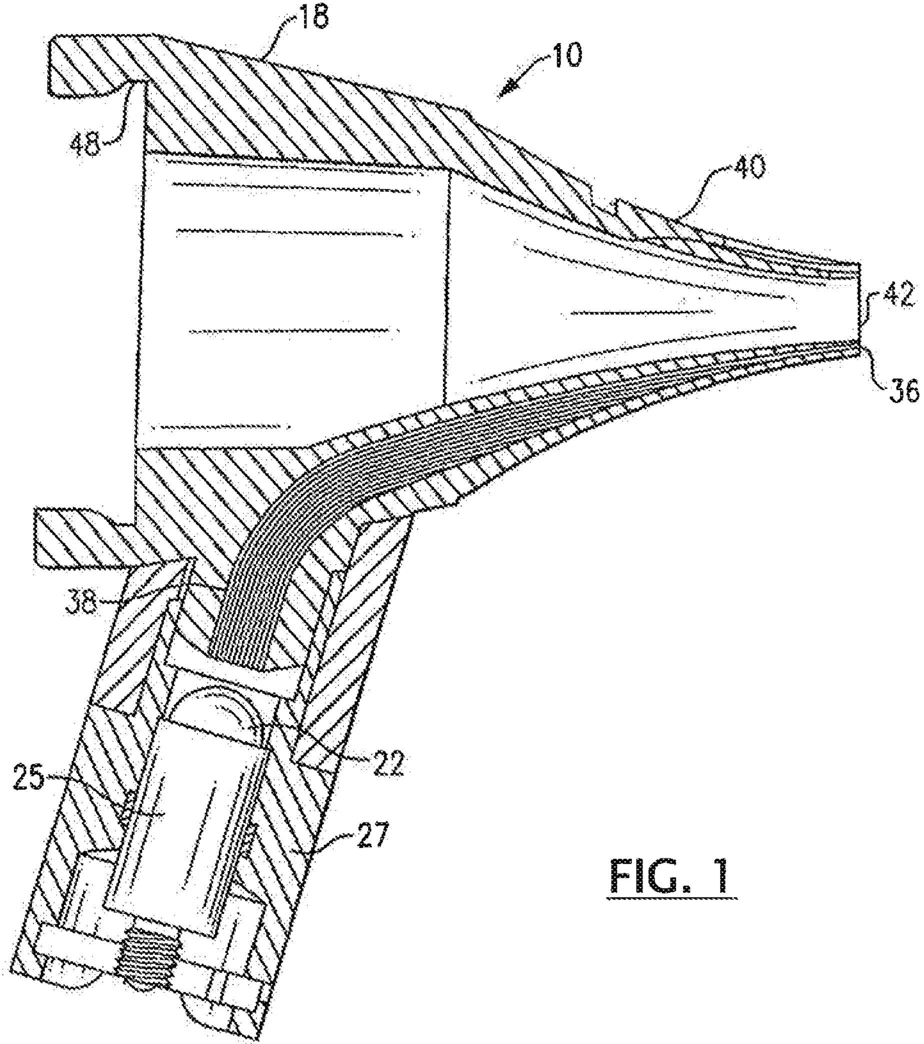
FIG. 1 is a partial side cross-sectional view of a head of an exemplary hand-held medical examination or diagnostic instrument.

A medical examination or diagnostic instrument can have a linear or near linear relationship between increments of the user controls and the measured light, such as by utilizing a linear relationship between the user controls and the voltage or the amperage powering the light source. However, the relationship between Perceived Light and Measured Light described by Equation 1 shows how such a system can lead to difficulties in obtaining a desired illumination level of a subject, due to high sensitivity of the perceived illumination to changes in the controls operated by a user at low illumination and low sensitivity at high illumination. Accordingly, it can be desirable to "linearize" the relationship between the user controls and the perceived illumination.

Linearizing the relationship between the user controls and the perceived illumination can provide more intuitive control of the illumination of a subject through the entire range of light output of a medical examination or diagnostic instrument. In an embodiment, the range of light output can be from a minimum light output to a maximum light output. In an embodiment, the minimum light output can be approximately 30% or less of the maximum or approximately 20% or less of the maximum or approximately 10% or less of the maximum or approximately 5% or less of the maximum or approximately 2% or less of the maximum. In some embodiments, a linearized relationship between the user controls and the perceived illumination can be achieved where a ratio of perceived incremented light output to the incremented user input signal is approximately a constant over the range. In particular embodiments, the ratio can vary from a constant over the range by approximately 30% or approximately 20% or approximately 10% or approximately 5% or less. In some implementations of a linearized relationship between the user controls and the perceived illumination, an algorithm can be followed, with examples of algorithms including linear (also referred to as "simple"), logarithmic or exponential, and multi-slope linear. An equation related to Equation 1 that relates the adjustment of the light output to the perceived light output is shown below as Equation 2, and implementations of a linearized relationship between the user controls and the perceived illumination can approximate the relationship of Equation 2, such as to within approximately 30% or approximately 20% or approximately 10% or approximately 5% or less:

$$\text{Perceived Light Output} = 100(\text{User Input Signal}/100)^{1/2} \qquad \text{(Equation 2)}$$

where,

Perceived Light Output is expressed in percent of maximum, and

User Input Signal is expressed in percent of maximum.

Equation 2 has combined Equation 1 with a linear relationship between the user input signal and the measured light source. Additional embodiments can combine Equation 1 with a different relationship between the user input signal and the measured light source to generate further embodiments of equations for linearization of the relationship between the user controls and the perceived illumination as described herein and can be implemented by any of the methods and equipment described herein.

The linearization and/or algorithm can be implemented in an instrument head and/or a handle, by any desired technique, such as mechanically, by way of a control circuit, by way of an algorithm or a combination of these techniques. In some embodiments, the implementation can include one or more processors or microprocessors that run an algorithm as described herein.

Medical care products, such as those used by general practitioner doctors, specialist doctors, other doctors and non-doctors (including physician assistants, nurses, opticians, office personnel, etc.) including both newer and older (including analog and digital) medical examination or diagnostic devices are generally a head and handle configuration. While this is convenient to the care giver, this may result in a significant amount of compatible systems and component parts (such as various heads and various handles), some of which might only be compatible with only some of the others or have differences in the control characteristics of the light intensity (such as where the rate of change in the light output as a function of a change in the control setting is different when a different head is attached to a handle or a different handle is attached to a head. In contrast, it is desirable all combinations of instrument heads and handles to be compatible with each other, such as for an older or an analog handle and a newer or a digital ophthalmoscope and otoscope head or an older or an analog ophthalmoscope and otoscope head and a newer or a digital handle (or new handles and legacy (older) instrument heads, or new instrument heads and new handles, or digital handles and analog heads or digital heads and analog handles) to be compatible with each other and to provide a mechanism to provide controls such that as many systems combinations as possible can be used together and/or can dim in an exponential or logarithmic (exponential and logarithmic being related functions, where one uses output of the other as the input to describe the same mathematical relationship, also referred to as the "inverse" of one another) fashion or otherwise to look more linear in the brightness response to the controls as perceived to the human eye. It can also be desirable to have similar control characteristics for different combinations of head and handle. While this formula of Equation 1 is fairly well known, an implementation as described here applies an exponential or logarithmic dimming across a stable, easily adjustable portion of a plurality of older handles that do not provide a linear perceived brightness response, and can lock to a low light level or to a full on and/or can even move through a steep slope of rheostat position vs output on an especially electrically unstable medical examination or diagnostic device handle. In an embodiment, a stable light output can be a light output that does not appear to flicker to a viewer. In an embodiment, stable light output can occur when the light modulation is not more than about 15% or about 10% or about 7% or about 5%, or about 3% or about 1.5% at a frequency range of the of about 3-65 Hz, or not more than about 10% at a frequency range of about 2-110 Hz., or not more than about 10% at a frequency range of about 1-10 kHz, meaning that the measured light output does not increase or decrease, such as by fluctuation, of more than the stated modulation amount over the stated frequency range. Light output stability issues can be more pronounced with LED illumination sources as compared to incandescent sources, and light output stability issues can be more pronounced with systems that include voltage regulation. Stability risk for LED illumination sources can be viewed as being greater, for example, when stability problems will occur at a broader range of frequencies, or at higher frequencies (especially within the range of 3-65 Hz), or at higher power levels or with greater light modulation at a given frequency or power level. Additionally, implementations can have other types of dimming across a stable, easily adjustable portion of a plurality of legacy handles as described herein to achieve a more linear perceived brightness response of the instrument, as an alternative to exponential or logarithmic dimming or in combination with exponential or logarithmic dimming and can be used where an exponential or logarithmic dimming are described. In addition, it can be desirable to have a way of the handle to identify the illumination characteristics (such as the relationship between a user input signal and the light, e.g. measured light, produced by the light source) are associated with the head and/or the head to identify the illumination characteristics the controls of the handle are associated with. In some situations, such as where both the head and the handle are capable of multiple illumination characteristics (such as the handle being compatible with an LED and a halogen light source, or the head being compatible with a handle having an LED driver and a halogen-only handle), it can be desirable for the head and the handle to negotiate operating illumination characteristics for the pairing. An example handle may provide compatibility with LED and halogen illumination and may have an LED driver and may provide stops in the mechanical rotation of the rheostat (or rotation or adjustment of another control, such as dial(s), slider(s) or button(s) or provide smooth movement of the control) that may result in accurate, repeatable light levels of the system.

An example may be that a new ophthalmoscope (or other instrument) head may accept all compatible handles, including old (legacy) handles that that will control the voltage to the instrument head in a linear fashion so the instrument head may receive the linear voltage, but the new instrument head then drives the instrument head's light output exponentially or logarithmically resulting in a smooth observed dimming of the medical examination or diagnostic instrument which approximates a linear result to the user's eye. The example handle may provide mechanical set points in the control such that a user easily identifies the "on" position and incremental light output settings that can be exponentially or logarithmically distributed for various legacy heads (such as older heads and/or heads that do not provide a linear perceived brightness response to the linear voltage control of the handle) or new heads, but the use of the new instrument head can result in the control being well regulated and this output to the new instrument heads as well as the new head's light output, may result in an approximately linear perceived brightness response to the controls.

Another example may be a new handle may accept all compatible instrument heads, including old (legacy) instrument heads. When an old (legacy) instrument head is connected to an old (legacy) handle, the linear voltage delivered by the handle to the instrument head is then delivered to the light source with the measured light varying approximately linearly with the voltage. When the old (legacy) instrument head is connected to the new handle, the voltage delivered to the instrument head will vary nonlinearly to provide a linear perceived brightness response from the light source to the controls.

The example handle may have a processor, microcontroller or control circuit that may detect the instrument head that is connected by the 'turn on' profile and accurately control the instrument head. The control may ensure a stable, repeatable low light level setting and exponentially or logarithmically increasing light levels which approximate a linear result to the user's eye. The example handle may mechanically provide a click or stop such that a user can easily have an obvious tactile feedback and repeatedly set a desired light level.

In embodiments, instrument heads may have a processor or microcontroller or control circuit that may detect the handle that is connected and control their light output to ensure stability, accuracy and exponentially/logarithmically increasing light output so no matter which handle is connected, the user may experience stable and repeatable low light levels as well as simple light level adjustment. Both the handles and heads will identify and accurately control low light levels such that there is a wide, stable control between lowest level and off.

In embodiments, both the handle and the instrument head may each independently have a processor or microprocessor or control circuit, with the control of the light output being performed as described herein by the processor, microprocessor or control circuit of only one of the instrument head and handle or of both of the instrument head and handle. In additional embodiments, only the instrument head or only the handle may have a processor or microprocessor or control circuit, with the control of the light output being performed as described herein by the processor, microprocessor or control circuit.

One step of implementing such a control scheme will for any instrument head or handle that includes a processor, microprocessor or control circuit to determine the characteristics of the part that it is paired with and whether the other paired part also includes a processor, microprocessor or control circuit for control of light output. Another step of implementing such a control scheme will be to adjust one or more power parameters for power delivered to an illumination source in response to a user control input. These steps of the control scheme are discussed in more detail below in reference to FIGS. 8-12.

The techniques described herein may be performed by a system and/or apparatus having non-transitory computer-readable media storing computer-executable instructions that, when executed by one or more processors, performs the method described herein.

Figure 2:
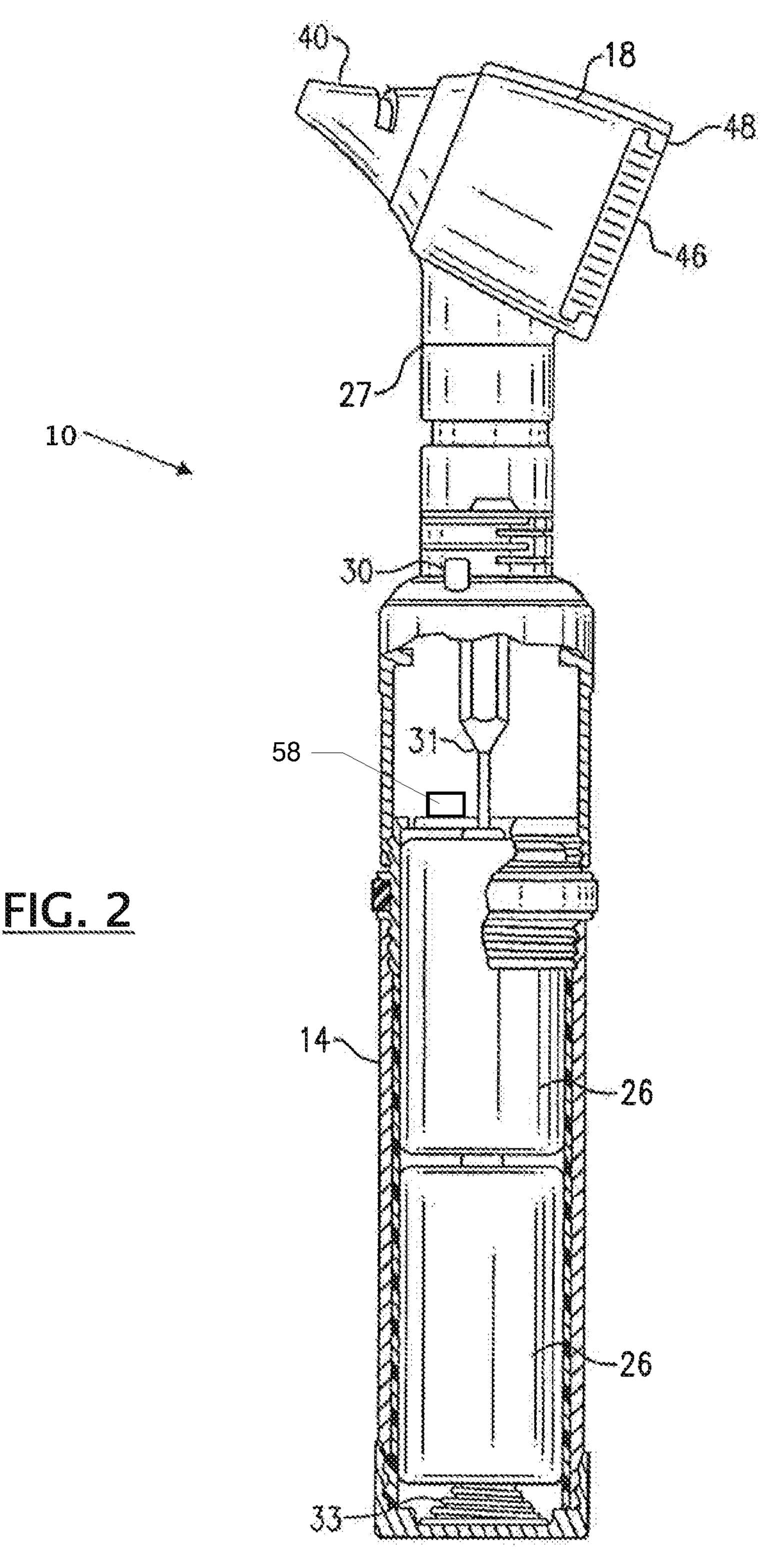
FIG. 2 is a partial side cross-sectional view of the instrument of FIG. 1.
Figure 3:
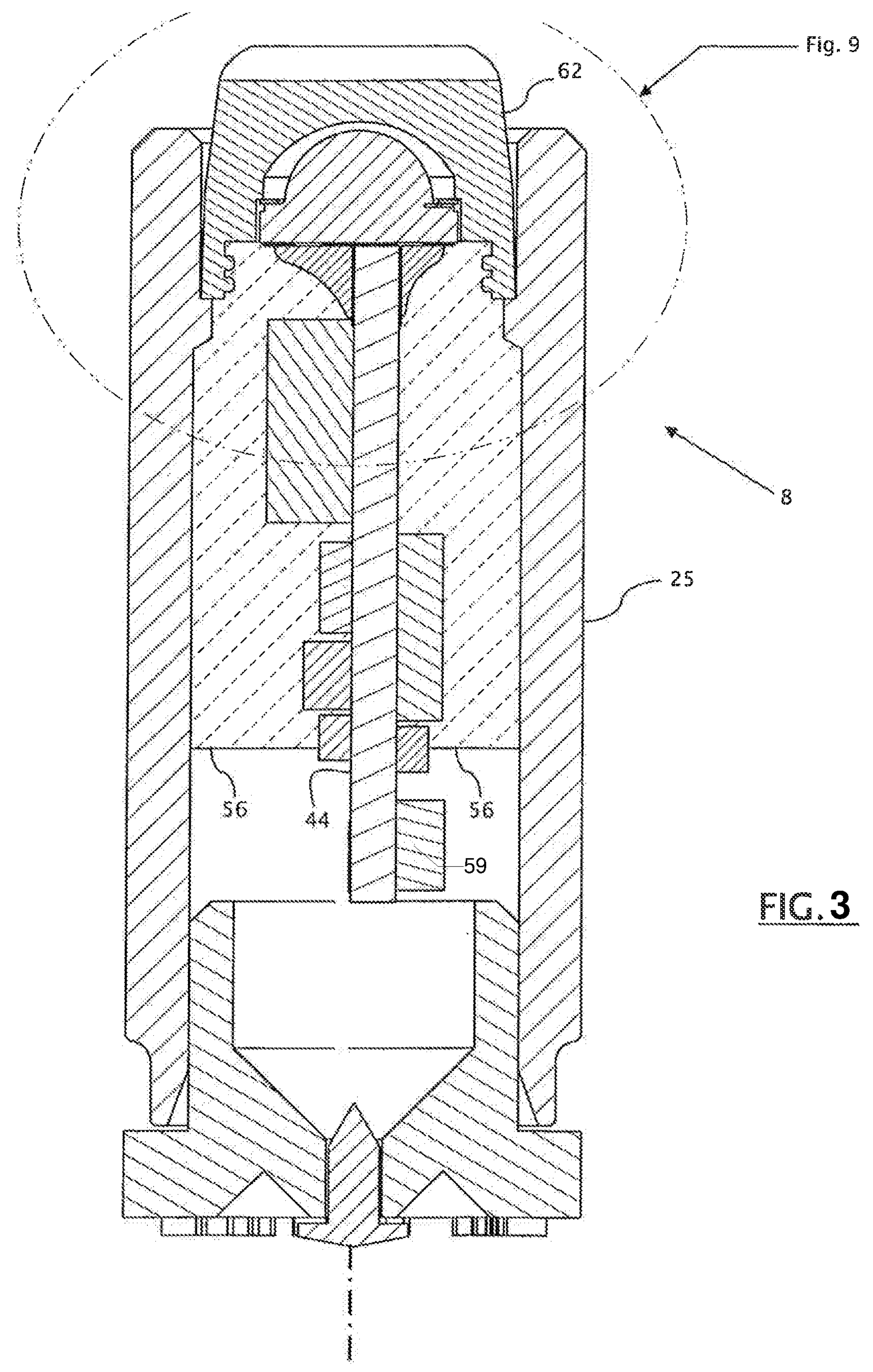
FIG. 3 is a cross-sectional view of a replacement light assembly according to an exemplary embodiment of the present disclosure.
Figure 4:
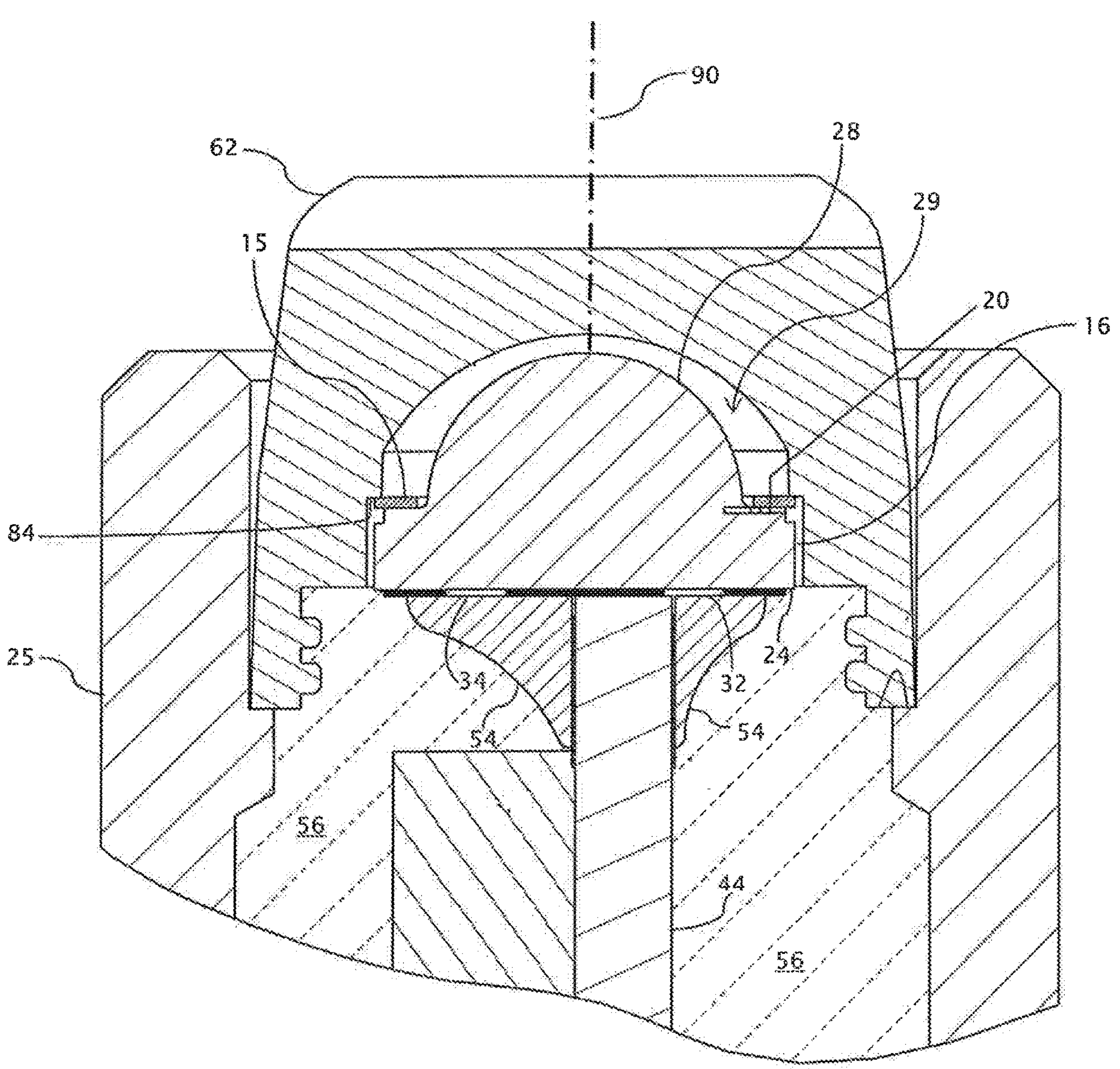
FIG. 4 is an enlarged view of a portion of the assembly illustrated in FIG. 3.
Figure 5:
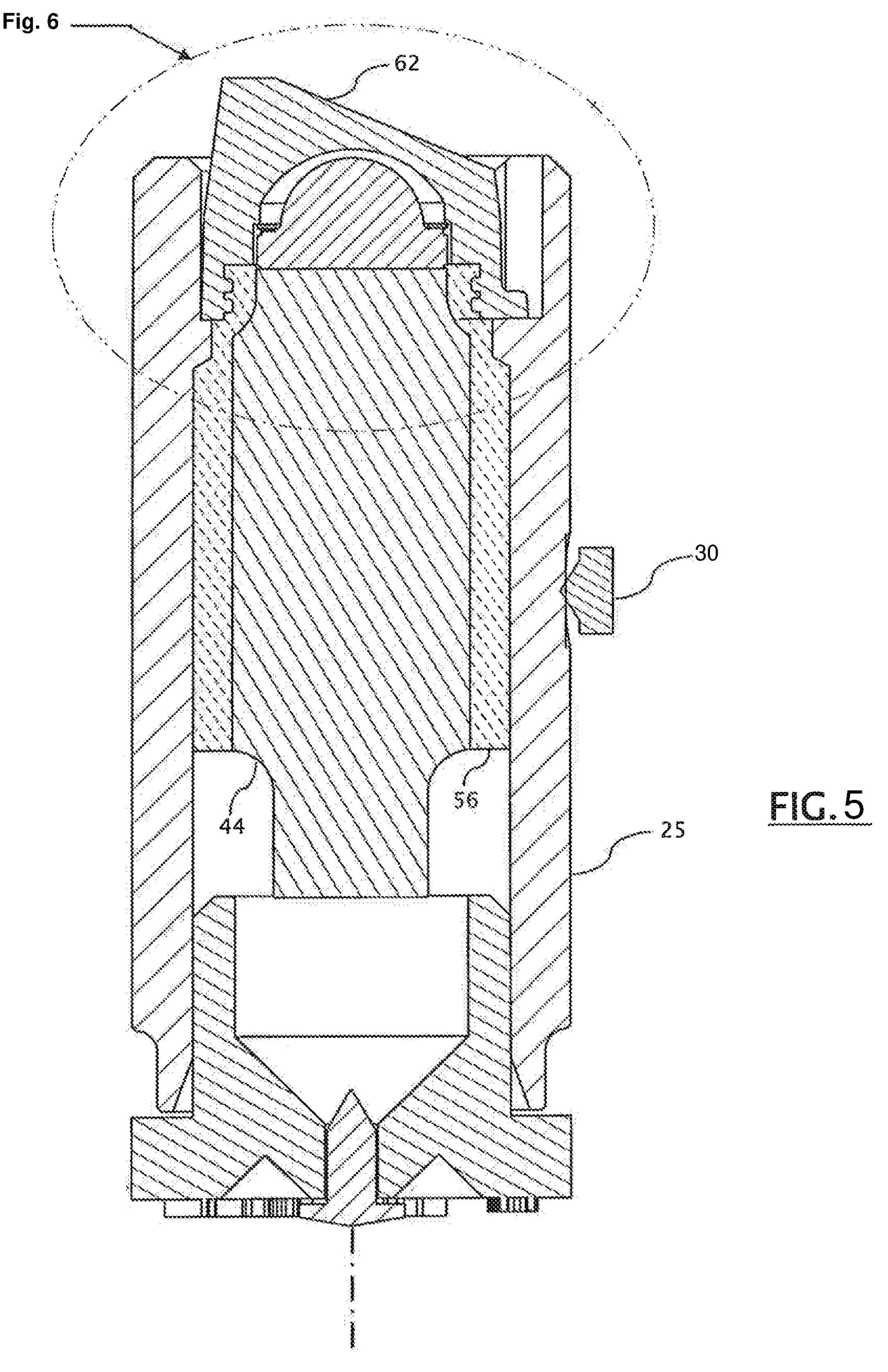
FIG. 5 is another cross-sectional view of the assembly shown in FIG. 3.
Figure 6:
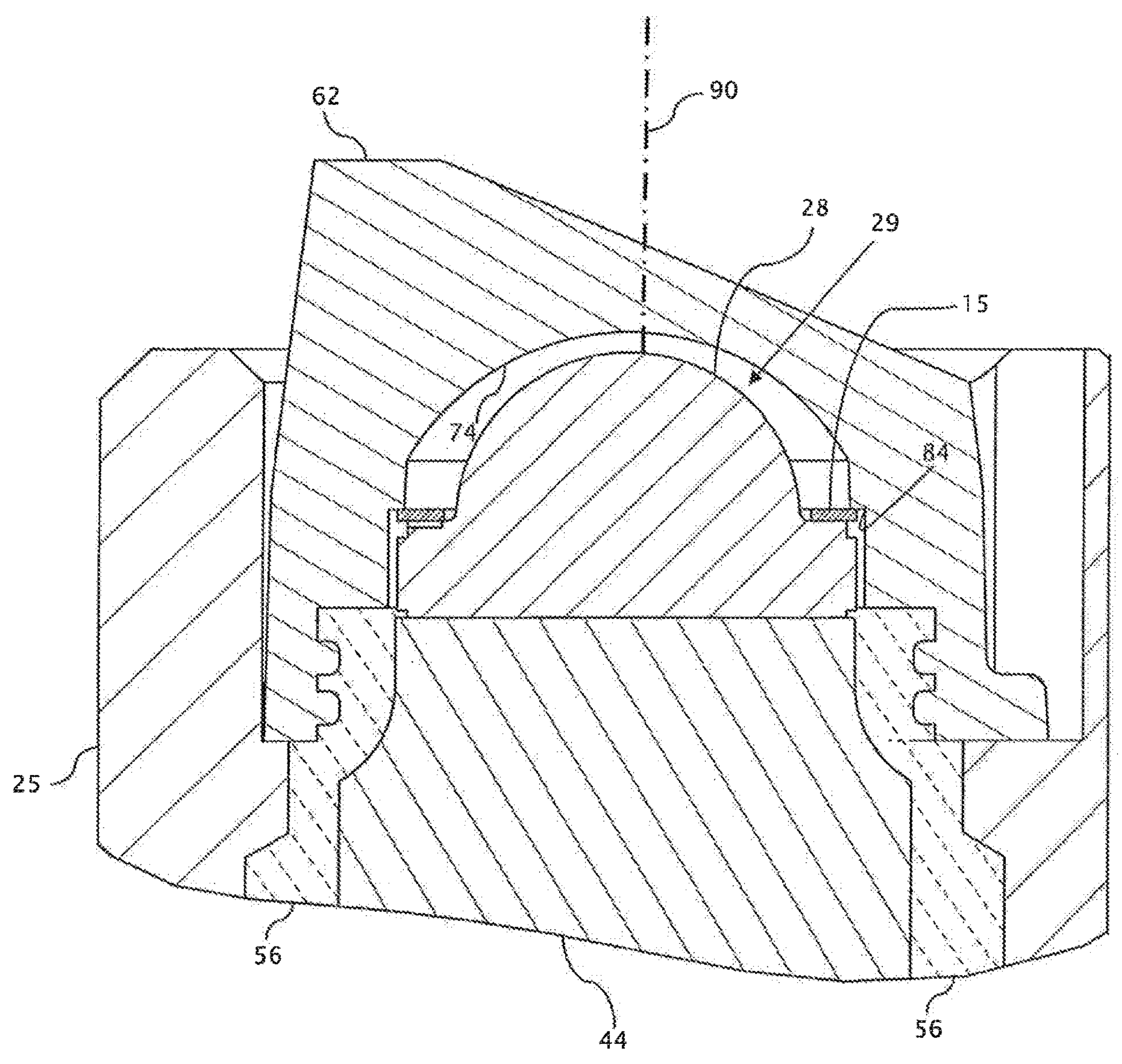
FIG. 6 is an enlarged view of a portion of the assembly shown in FIG. 5.

FIGS. 1 and 2 illustrate a hand-held medical examination or diagnostic instrument 10 according to an exemplary embodiment of the present disclosure. Embodiments of the present disclosure may be utilized with any of a variety of hand-held medical examination or diagnostic instruments such as, for example, ophthalmoscopes, otoscopes, sigmoidoscope, and the like. For ease of description, however, an exemplary otoscope shall be described for the duration of this disclosure unless otherwise noted, with the description, operation and control features being applicable to other medical examination or diagnostic instruments as well.

As shown in FIGS. 1 and 2, the medical examination or diagnostic instrument 10 may include an instrument head 18 attached to the top of a handle 14. The handle 14 and/or the instrument head 18 may be substantially hollow, and the instrument head 18 may include a frustoconical tip portion 40 onto which a disposable speculum (not shown) may be fitted in a conventional manner. In an exemplary embodiment, the speculum may be sized, shaped, and/or otherwise configured to fit a predetermined distance into an ear canal of a patient so that, for example, the tympanic membrane or other medical target may be examined. The tip portion 40 may have an opening 42 at the distal end thereof, and an eye piece 46 may be attached to the proximal end 48 of the instrument head 18 to assist in such examination. Accordingly, in an exemplary embodiment, the eye piece 46 may form part of an optical path with the opening 42 through the hollow instrument head 18 to permit viewing of a medical target. While the tympanic membrane may be one such target, it is understood that other exemplary medical examination or diagnostic instruments 10 may be utilized to view other like membranes or targets. Such exemplary medical targets may include portions of the eye, nose, throat, and/or other portions of the human anatomy.

Exemplary medical examination or diagnostic instruments 10 may employ, for example, an incandescent lamp 22, such as, for example, a halogen or xenon lamp (but other light sources can be used as described herein, with the description, operation and control features being applicable to these other light sources as well.) At least a portion of such an incandescent lamp 22 may be mounted to, retained within, and/or otherwise associated with a housing 25 disposed within a base 27 or other portion of the instrument head 18. The incandescent lamp 22 may be functionally, electrically, and/or otherwise operably connected to a power supply within the medical examination or diagnostic instrument 10 or to an external power supply. For example, the incandescent lamp 22 may be electrically connected to one or more batteries 26 retained in a compartment of the instrument handle 14. Alternatively, the instrument handle 14 and/or other portions of the medical examination or diagnostic instrument 10 may be electrically connected to a conventional wall outlet or other similar power supply via an electrical cord (not shown) or other like connection. It is also understood that the medical examination or diagnostic instrument 10 may employ one or more springs 33, pins 31, controls 30, and/or other components to assist in maintaining an effective electrical connection between the incandescent lamp 22 and the power supplies discussed above. Such components may also assist in controlling, for example, the current, polarity and/or voltage supplied to the incandescent lamp 22.

In an exemplary embodiment in which the medical examination or diagnostic instrument 10 comprises an otoscope, the instrument 10 may also include a bundle of optical fibers 38 extending from proximate the incandescent lamp 22, through the base 27 of the instrument head 18, to a bundle of light transmitting ends 36 or other optical means that are disposed at the distal opening 42. The optical fibers 38 and the transmitting ends 36 may be configured to illuminate the medical target during examination.

Alternatively, in an exemplary embodiment in which the medical examination or diagnostic instrument 10 comprises an ophthalmoscope, the bundle of optical fibers 38 may be omitted. Instead, in such an exemplary embodiment, the medical examination or diagnostic instrument 10 may further comprise one or more collimating lenses, reticles, positive lenses, negative lenses, mirrors, and/or other optical or beam shaping components to direct radiation emitted by the incandescent lamp 22. For example, an exemplary ophthalmoscope may include a mirror that is offset from, for example, a central or optical axis 90 of the incandescent lamp 22. Such a mirror may be configured to direct radiation emitted by the incandescent lamp 22 in the direction of the medical target optically downstream of, for example, a reticle of the ophthalmoscope. Such mirror positioning may be required due to, for example, the configuration of the ophthalmoscope head 18. To compensate for such off-axis or offset mirror positioning, the exemplary ophthalmoscope may further employ one or more prisms, wedges, and/or angled optical components optically downstream of the incandescent lamp 22 to direct light and/or other radiation emitted by the incandescent lamp 22 in the direction of the offset mirror.

In still another exemplary embodiment in which the medical examination or diagnostic instrument 10 comprises an ophthalmoscope, the offset mirror described above may, instead, be substantially aligned with, for example, the central or optical axis 90 of the incandescent lamp 22. In such an exemplary embodiment, one or more of the optical components described above for shifting and/or angling light emitted by the incandescent lamp 22 in the direction of the mirror may not be required.

FIGS. 3 through 6 illustrate an exemplary light assembly 8 of the present disclosure in which the incandescent lamp 22 has been replaced by a different light source such as, for example, an LED. Such an exemplary light source 12 is illustrated in greater detail in FIG. 7, and the light source 12 may comprise an LED, a low-intensity laser, and/or any other light source known in the art. For ease of description, however, an exemplary embodiment in which the light source 12 comprises an LED shall be described for the duration of this disclosure unless otherwise noted, with the description, operation and control features being applicable to other light sources as well.

The incandescent lamp 22 discussed above can be replaced with one or more LEDs to illuminate a medical target during examination. Replacing an incandescent lamp 22 with an LED in this way may improve, for example, the durability, illumination, and/or other qualities of the instrument 10, and thus may be desirable in modern hand-held or non-hand-held medical examination or diagnostic instruments 10. In replacing an incandescent lamp 22 with an LED, one or more lenses or other additional optical components may be employed to shape the light emitted by the LED. Such components may bend, shift, collimate, focus, and/or otherwise shape the radiation emitted by the LED to substantially match the optical characteristics of the incandescent lamp 22 such that the functionality of the medical examination or diagnostic instrument 10 may remain substantially unchanged.

In an exemplary embodiment, the light assembly 8 may include a light source 12 mounted to a substrate 16, and a circuit board 44 disposed inclined to the substrate 16. The assembly 8 may also include first and second connectors 54 mounting and electrically connecting the circuit board 44 to the substrate 16. Such an exemplary light assembly 8 may further include one or more heat sinks, and a thermal conductor 56 thermally connecting at least one of the heat sinks to the substrate 16.

In an exemplary embodiment, the substrate 16 may be constructed from plastics, polymers, and/or other typical circuit board material, and may comprise a printed circuit board. For example, the substrate 16 may include one or more electrical terminals embedded therein and/or otherwise formed thereon. Exemplary electrical terminals 32, 34 may be positive and negative electrical terminals, respectively. Such electrical terminals 32, 34 may be electrically and/or otherwise operably connected to one or more components disposed on the substrate 16. For example, the electrical terminals 32, 34 may be configured to provide and/or otherwise direct an electrical current, polarity and/or voltage from a power source, such as the batteries 26 of the medical examination or diagnostic instrument 10, to the light source 12 mounted on the substrate 16. As shown in at least FIGS. 4 and 6, the substrate 16 may have a top surface 20 and a bottom surface 24. In an exemplary embodiment, the light source 12 may be disposed on and/or otherwise mounted to the top surface 20, and the bottom surface 24 may define and/or otherwise include the electrical terminals 32, 34 discussed above.

Figure 7:
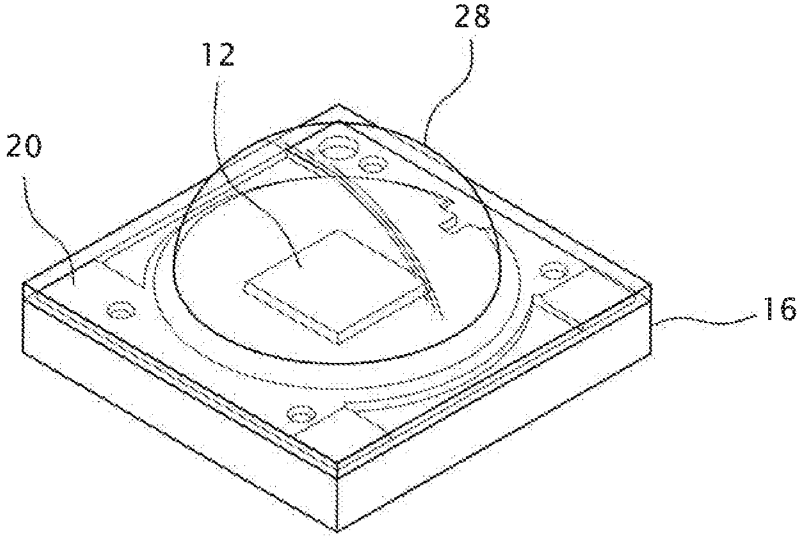
FIG. 7 is an isometric view of a light source and a substrate according to an exemplary embodiment of the present disclosure.

As shown in greater detail in FIG. 7, a cover 28 may be mounted on and/or otherwise connected to the substrate 16. The cover 28 may be, for example, substantially transparent to permit light and/or other radiation emitted by the light source 12 to pass through the cover 28 to a lens 62 of the light assembly 8. The cover 28 may have any shape, size, and/or other configuration known in the art. For example, the cover 28 may be substantially convex, and may act as a positive lens. In such an exemplary embodiment, the cover 28 may assist in collecting and/or otherwise focusing divergent light emitted by the light source 12.

Alternatively, the cover 28 may be substantially planar, thereby providing substantially no added intensification of the emitted light. In still another exemplary embodiment, at least a portion of the cover 28 may be substantially concave and may act as a negative lens. In such an embodiment, the concave portion of the cover 28 may act as a negative lens and may assist in further diverging the light emitted by the light source 12. The light emitted by the light source 12 may pass through an air gap 29 between the cover 28 and the lens 62 before reaching the lens 62.

The lens 62 may have any shape, size, and/or other configuration known in the art to assist in bending, shifting, angling, shaping, focusing collimating, and/or diverging the light emitted by the light source 12 optically upstream of the other optical components of the medical examination or diagnostic instrument 10. For example, the lens 62 may be shaped, sized, and/or otherwise configured to modify the path, orientation, intensity, and/or other optical characteristics of the light emitted by the light source 12 to substantially match the corresponding optical characteristics of the radiation emitted by an incandescent lamp 22 previously employed by the medical examination or diagnostic instrument 10. Thus, the combination of the lens 62 and light source 12 (or in some embodiments the light source 12 alone) may be utilized as a direct replacement for incandescent lamps 22 commonly used in otoscopes, ophthalmoscopes, vaginascopes, dermatoscope, transilluminator, endoscope, sigmoidoscope, anoscope, retinoscope, general viewing scope and other hand-held and non-hand-held medical examination or diagnostic instruments 10. Due to the configurations of the light source 10 and the lens 62, these components may replace such incandescent lamps 22 without further modifications to, for example, the light assembly 8 or other hand-held medical examination or diagnostic instrument components.

The lens 62 may be fixed relative to the light source 12 in order to maintain the desired beam-shaping effect on the light emitted by the light source 12. In an exemplary embodiment, the lens 62 may be mounted on and/or otherwise connected to the substrate 16 by any known means. For example, an adhesive 15 may be disposed between, for example, one or more mounting surfaces 84 of the lens 62 and the top surface 20 of the substrate 16. Alternatively, at least a portion of the lens 62 may be molded onto the substrate 16. In still a further exemplary embodiment, the lens 62 may define one or more grooves, clips, slots, notches, shoulders, and/or other known retention components to assist in fixedly disposing the substrate 16 relative to the lens 62.

In embodiments, the medical examination or diagnostic instrument 10 may utilize different instrument heads 18 with different handles 14. Thus, it may be necessary for the instrument head 18 to determine which type of handle 14 to which it is operatively connected. Likewise, it may be necessary for the handle 14 to determine which instrument head 18 or which light source 12 to which it is operatively connected. In configurations, the instrument head 18 may include a processor or microcontroller or control circuit 59 that may detect the handle 14 to which the instrument head 18 is operatively connected.

In configurations, a processor (this discussion of the processor will also apply to the use of a microprocessor or control circuit) 59 in the instrument head 18 may identify the base the determination of the type of handle on a characteristic of the handle, for example, one or more electrical characteristics of the handle, such as a polarity of the power connectors of handle 14, that is detected by the instrument head 18 or experienced by the instrument head 18 after connection to the handle 14. Additional characteristics of the handle 14 that may be measured and/or used by the processor in the instrument head are the voltage being supplied by the handle 14, the voltage stability of the power supplied by the handle 14, a wave form of the power supplied by the handle 14, a derived characteristic of the voltage supplied by the handle 14 (such as the derivative of voltage with respect to time or the second derivative of voltage with respect to time), or another electrical characteristic of the power supplied by the handle 14. One way of evaluating voltage stability can be to measure the change in voltage of the handle output, both under load and without load, with the "load" being, for example, a resistor being applied to current from the handle 14. In some configurations, the polarity or other characteristic(s) of the handle 14, or the type of handle 14 itself, can be stored in memory of the handle 14 and then read and used by the processor 58 in the handle 14 or read and used by the processor 59 in the instrument head 18.

Figure 8:
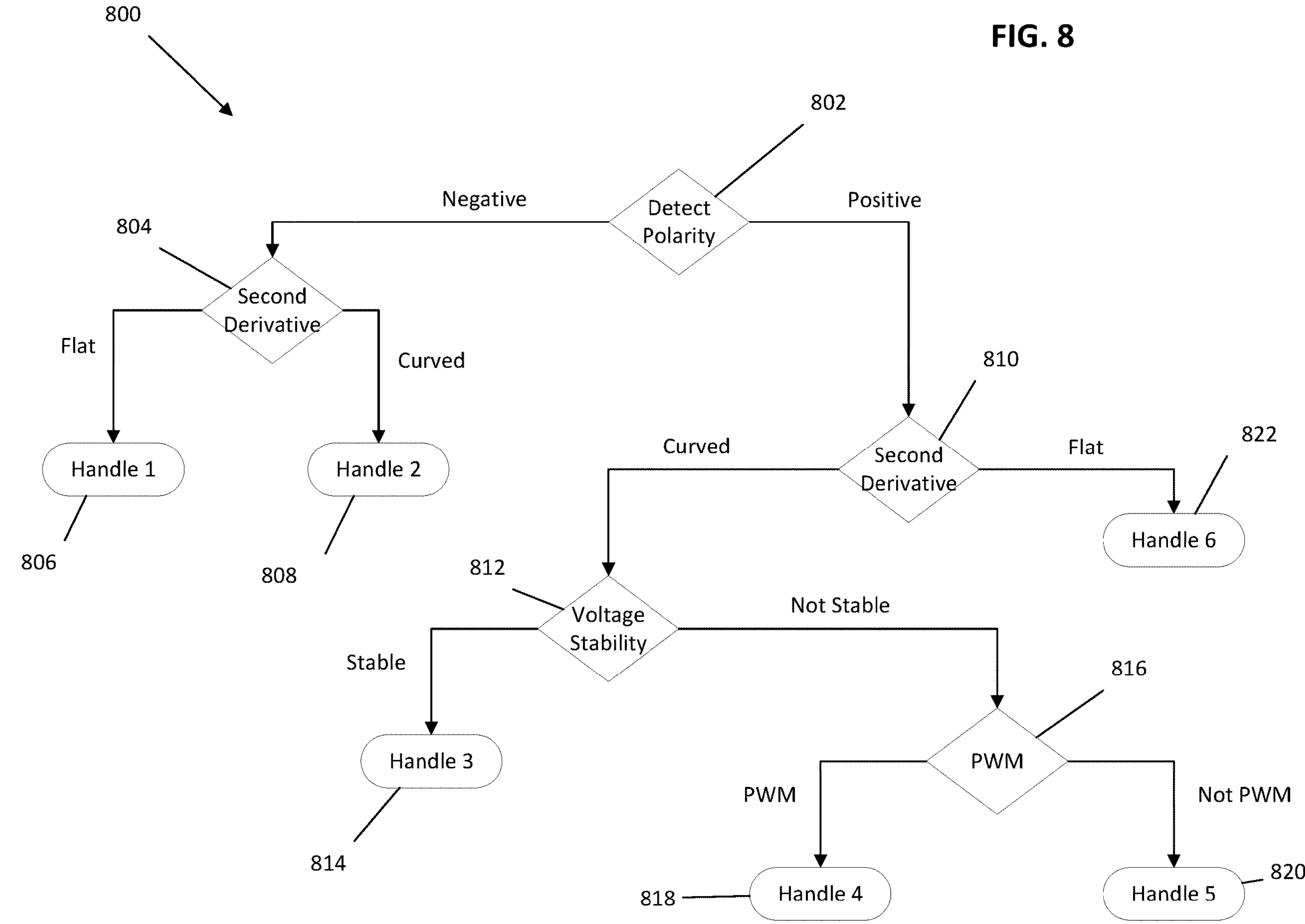
FIG. 8 is a flow diagram of an example method for identifying a handle of a medical examination or diagnostic instrument.

An example a method 800 of the determination of the type of handle by the instrument head is presented in FIG. 8, where at 802 the instrument head 18 may detect whether the polarity of the handle 14 is negative or positive. If the detected polarity is negative, then at 804 the instrument head 18 may perform a second order comparison that evaluates an additional parameter, such as the second derivative of voltage with respect to time. If, for example, the second derivative of voltage with respect to time is flat (approximately constant), then at 806 the processor 59 of the instrument head 18 may determine that the handle 14 is a first handle type (for example, a handle with a wall-mounted regulated power supply, with negative polarity, a medium risk of stability problems with LED light output, stable voltage range and a logarithmic response, and without a processor 58, such as a Welch Allyn CIWS handle.) However, if, for example, at 804 the second derivative of voltage with respect to time is curved, then at 808 the processor 59 of the instrument head 18 may determine that the handle 14 is a second type of handle (for example, a handle with a wall-mounted regulated power supply, negative polarity, high risk of stability problems with LED light output, high voltage range and a logarithmic response, and without a processor 58, such as a Welch Allyn 767 handle.)

However, if, for example, at 802 the detected polarity is positive, then at 810 the processor 59 of the instrument head 18 may perform a second order comparison that evaluates an additional parameter, such as the second derivative of voltage with respect to time. In some examples, the second order comparison performed by the processor 59 of the instrument head 18 may be substantially similar to and/or the same as the comparison performed at 804. In two embodiments, the second order comparison can determine that the result of the second derivative of voltage with respect to time can be flat or curved. If, for example, the result is determined to be flat (approx. constant), then the processor 59 of the instrument head 18 determines that the instrument head is operatively coupled to a handle of the sixth type at 822 (for example a handle with a wall-mounted regulated power supply, positive polarity, high risk of stability problems with LED light output, unstable voltage range and a multi-slope linear output, such as a Welch Allyn 777 handle.) If, for example, the result at 810 is curved, then at 812 a further check can be performed. At 812, the processor 59 of the instrument head 18 may perform a further check, such as a voltage stability test where the voltage provided by the handle 14 is measured with load and without load. In an embodiment, for the measurement with load, the current can be applied to a resistor, and the voltage measured and compared to a separate measurement without the resistor. In an embodiment, a stable voltage can be one that remains within a voltage band. In another embodiment, a stable voltage can be one that does not fall more than a prescribed amount when the handle is placed under load. If stable voltage is detected, the processor 59 of the instrument head 18 may determine that the handle 14 is a third type at 814 (for example, a handle with a positive polarity, low risk of stability problems with LED light output, precise voltage range and a linear response, with a processor.) If at 812 stable voltage is not detected with the handle placed under load, and the handle 14 is determined to not be a third type, then the processor 59 of the instrument head 18 may perform a second check at 816. For example, at 816 the processor 59 of the instrument head 18 may evaluate the type of signal used to deliver energy. Examples of type of signals include pulse width modulation (PWM, analog with variable current, analog with variable voltage. In an embodiment, at 816, the processor 59 can determine if PWM is detected, the handle 14 is a fourth type at 818 (for example, a handle with a Li-Ion battery, PWM dimming, positive polarity, medium risk of stability problems with LED light output, and a linear output, and without a processor, such as a Welch Allyn 719 handle) or a fifth type at 820 if PWM is not detected (for example, a battery powered handle with resistive dimming, positive polarity, stable operation, and a logarithmic output, and without a processor, such as a Welch Allyn 710 handle.)

In embodiments of a handle 14 that includes a processor 58, microprocessor or control circuit (i.e., that provides a linear perceived brightness response from the light source to the controls), such as a third type handle, it can be desirable to also provide an option to bypass this processor 58, microprocessor or control circuit in the handle 14. Such a bypass can, for example, allow the illumination control to be by the instrument head 18 without relying upon control by the handle 14. Such a configuration can allow the instrument to rely upon a processor 59, microprocessor or control circuit located within the instrument head 18 instead of by the processor 58, microprocessor or control circuit located within the handle 14.

Figure 10:
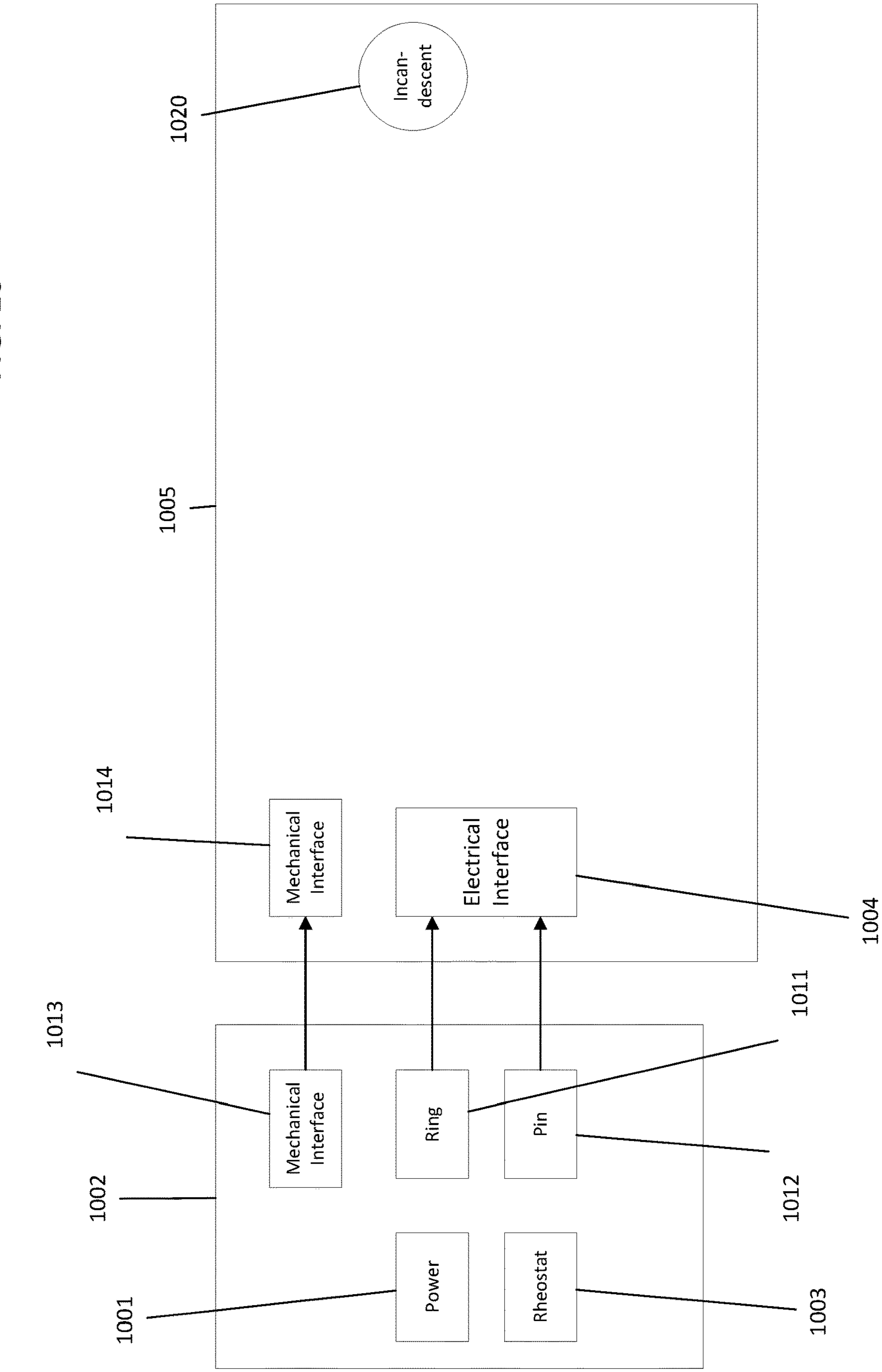
FIG. 10 schematically illustrates another example electrical and software system for an instrument head of a medical examination or diagnostic instrument.

An example of the determination of the type of instrument head 18 that can be performed by a handle 14 can be to measure the type of load that the instrument head 18 applies through the electrical connectors of the handle 14. In an embodiment, a load can be a resistive load or a load that is approximately entirely resistive, indicating an instrument head of a first type. An instrument head of a first type may indicate an instrument head that does not provide an electrical connection to the light source 12 through a processor, microprocessor, control circuit or LED driver, and may connect to an incandescent bulb 1020 (such as a halogen bulb), as shown in FIG. 10. A different type of load than the resistive load described above can indicate the presence of a processor, microprocessor or control circuit is present and that the instrument head is a second type, or can indicate an LED driver is present and that the instrument head is a third type. An embodiment of an instrument head 18 that includes a processor 59, microprocessor or control circuit (i.e., that provides a linear perceived brightness response from the light source to the controls) can be a type 2 instrument head. In embodiments of a type 2 instrument head, it can be desirable to provide an option to bypass the processor 59, microprocessor or control circuit in the instrument head 18 to allow the illumination to be controlled by the handle 14, such as by utilizing processor 58, microprocessor or control circuit located within the handle 14 instead of by utilizing the processor 59, microprocessor or control circuit located within the instrument head 18.

As a part of the operation of the medical examination or diagnostic instrument, a selection of the controlling element of the instrument might be performed, such as whether controls in the instrument head 18 or the handle 14 will have the role of adjusting the light output from the light source.

Based upon the determination as to which handle 14 the instrument head 18 is operatively coupled, the instrument head may control the light output of the light source 12 based on power received from the handle 14 or the handle 14 may control the light output of the light source 12 based upon power provided by the handle 14 and a characteristic of instrument head 18 present, such as light output characteristics of the light source 12 as a function of voltage, polarity, current, voltage stability, voltage wave form (e.g. AC, DC), power variation form (e.g. Pulse Width Modulation (PWM), voltage change, current change) or a combination thereof.

When an instrument head 18, but not the handle 14, includes a processor 59, microprocessor or control circuit (i.e., that provides a linear perceived brightness response from the light source to the controls), the processor 59 can determine that the processor 59, microprocessor or control circuit in the instrument head 18 for will control the light output.

When a handle 14, but not the instrument head 18, includes a processor 58, microprocessor or control circuit (i.e., that provides a linear perceived brightness response from the light source to the controls), the processor 58, microprocessor or control circuit in the handle 14 can control the light output.

When both the handle 14 and the instrument head 18 includes a processor 58, 59, microprocessor or control circuit (i.e., that provides a linear perceived brightness response from the light source to the controls), the processor 58 or the processor 59 or both the processor 59 and 58 can determine which processor 58, 59 microprocessor or control circuit to utilize for control of the light output. In some examples, a default of the processor, microprocessor or control circuit 58 in the handle 14 can be used. In some examples, a default of the processor, microprocessor or control circuit 59 in the instrument head 18 can be used.

Figure 9:
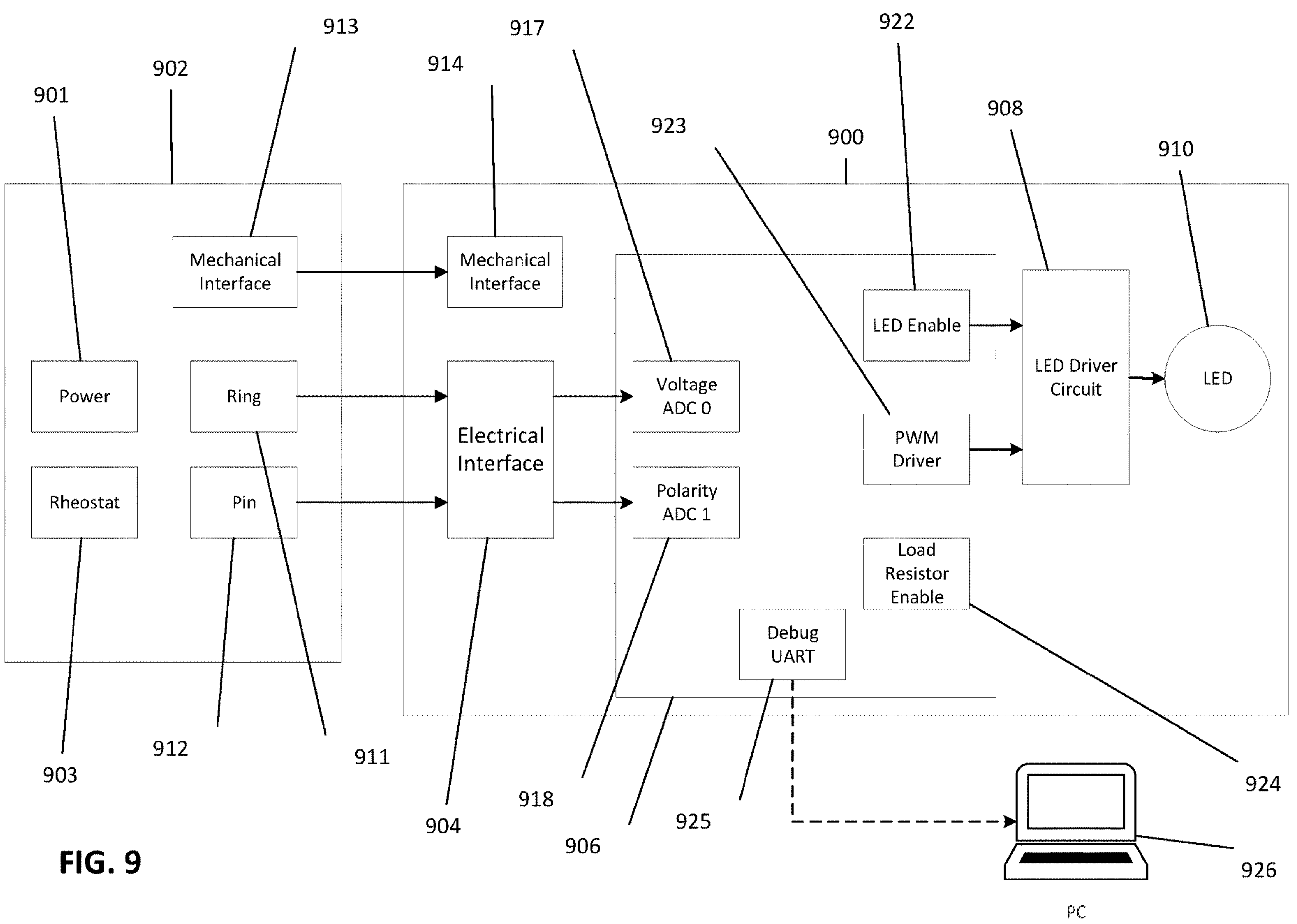
FIG. 9 schematically illustrates an example electrical and software system for an instrument head of a medical examination or diagnostic instrument.

FIG. 9 schematically illustrates an example electrical and software system 900 for the instrument head 18 or the handle 14. The system 900 is coupled to an energy source 902, e.g., an energy source of the handle 14 or battery, a power connection from another piece of equipment, AC adapter or USB power supply, etc., that can provide energy to the electrical and software system 900. Mechanical interface parts 913, 914 can attach or integrate the energy source 902 to the system 900. The energy source 902 can include a power switch 901 and a rheostat 903 or other user input device for providing a signal to increase or decrease the illumination from a light source 12, such as an LED 910. The illumination control system software 906 (which can be run on a processor or microprocessor 58, 59 or be wired into a control circuit) may determine the voltage, current, voltage stability, voltage wave form, power wave form and/or polarity received through an electrical interface 904 from the energy source 902 such as through ring 911 and pin 912 connectors. Signals related to electrical characteristics can be received, for example, via an analog-digital converter input for voltage at connector 917 and/or polarity at connector 918. The voltage, current, voltage stability, voltage wave form, power wave form and/or polarity may be utilized by an illumination control system software 906 to drive an LED driver circuit 908 to drive an LED light source 910 of the light source 12 in the instrument head 18. Also shown in FIG. 9 are an LED enable connector 922 to energize the LED driver circuit 908, a PWM driver connector 923 to facilitate variable output from a light source 12 such as an LED 910 or incandescent bulb 1020 (shown in FIG. 10.) Thus, the instrument head 18 may, based upon the detection of the type of handle 14 to which the illumination head 18 is operatively coupled, provide a smooth transition of power in perceived lighting response such that the illumination head 18 via the LED light 910 of the light source 12 may produce stable and steady low levels of emitted light to high levels of emitted light and may smoothly transition therebetween by reducing the suddenness of perceived dimming or brightening at the low end of the light output, such as by providing a more linear perceived brightness response from the light source to the controls. Also shown in FIG. 9 is a port 925 for debugging, maintenance, programming, etc. which can be used, for example for universal asynchronous receiver/transmitter communications with an external device 926, such as a computer, a laptop, a phone, or other communications or equipment diagnostic or maintenance device.

FIG. 10 schematically illustrates an example electrical system 1005 for an incandescent light source 1020 (such as a halogen bulb.) Here, an energy source 1002 with a power switch 1001, rheostat 1003 or other user input device for providing a signal to increase or decrease the illumination from a light source 12, such as an incandescent bulb 1020 provides power through, for example, a ring 1011 and pin arrangement 1012 to an electrical interface to the electrical system 1005. The energy source 1002 can be attached or integrated to the electrical system 1005 through mechanical interface parts 1013 and 1014. Power is routed to an incandescent bulb 1020 for illumination. Electrical system 1005 illustrates an example of an illumination system that provide light output that is approximately linear in the measured brightness response to the controls. In some embodiments the energy source can be an energy source of the handle 14 or battery, a power connection from another piece of equipment, AC adapter or USB power supply, etc., that can provide energy to the electrical system 1005. In an embodiment, an LED 910 and LED driver or driver circuit can be used in place of or with the incandescent bulb 1020. In an embodiment, a PWM driver or driver circuit can be included in the electrical system 1005 to be in electrical communication with the rheostat 1003 (or other control input) and the incandescent bulb 1020 or LED 910 to provide dimming of the light output.

In an embodiment, voltage values and/or current values output by the handles 14 and their energy sources 902, 1002 can be converted into PWM output values or current output values or voltage output values through multiple algorithms by the processor 59 of the instrument head 18 to which a handle 14 is operatively coupled or by the processor 58 of the handle. In an embodiment, algorithm running on the processor 58,59 can take an input signal related to the control position, such as a user input signal, and utilize the input signal to modulate an output voltage, an output current or an output PWM signal in relation to the input signal, with the output voltage, output current or output PWM signal being directed to increase, decrease, or hold constant the illumination of a light source 12. In an embodiment, the algorithm can include a module that converts an analog input signal, such as an analog input signal where the voltage or current or power is related to the control position, to a digital signal, such as a PWM signal where the magnitude of the analog input signal is related to the power carried by the PWM signal, such as by being related to the duty cycle of the PWM signal. In an embodiment, the algorithm can include a module that converts a digital signal, such as a PWM signal to an analog signal where the power carried by the digital signal is related to the power, the voltage or current of the analog signal. In an embodiment, the algorithm can include a module that converts a digital signal to another digital signal, such as converting a PWM signal to another PWM signal, where the power of the digital input signal is related to the power of the other digital signal. In an embodiment, the output voltage, output current or output PWM (or other digital) signal can be sent directly to the illumination source. In an embodiment, the output voltage, output current or output PWM (or other digital) signal can be sent directly to the illumination source can be sent to a driver or other circuit that modifies a voltage, current or power level of the output signal, such as by amplifying the power, before the signal is sent to the illumination source 12. In an embodiment, the algorithm can include a module that improves the stability of the light output, such as the light output of an LED illumination source. In an embodiment of a module that improves the stability of the light output, the module can, for example, increase the operating frequency, slow or dampen the rate of change of illumination, add capacitance to the input signal, limit the illumination range (such as by setting the minimum illumination at a higher level), add a resistive load in parallel to the output of the driver, etc. In an embodiment, a module that improves the stability of the light output can be used with a processor 58, 59, microprocessor or control circuit of an instrument head 18 or a handle 14 that utilizes or is connected to a component with a voltage regulator. In an embodiment, a module that improves the stability of the light output can be used with a processor 58, 59, microprocessor or control circuit of an instrument head 18 or a handle 14 that does not utilize and is not connected to a component with a voltage regulator. In embodiments, the algorithm can utilize one or more modules described herein.

In an embodiment, the algorithm may be selected for each energy source 902, 1002 based on dimming performance and stability and for the light source present in the instrument head 18, and can be tailored for specific handle and head combinations, such as for voltage differences, voltage stability, current limits, impedance, etc. In an embodiment, an algorithm can include a module that maintains or changes the response of the illumination source to the control position or input signal, such as by changing the sensitivity of the light output to changes in the control position at different control positions. For example, the perceived illumination by the illumination source 12 can be approximately linear with the control position. In an embodiment, the measured illumination by the illumination source 12 can be approximately linear with the control position.

Figure 11:
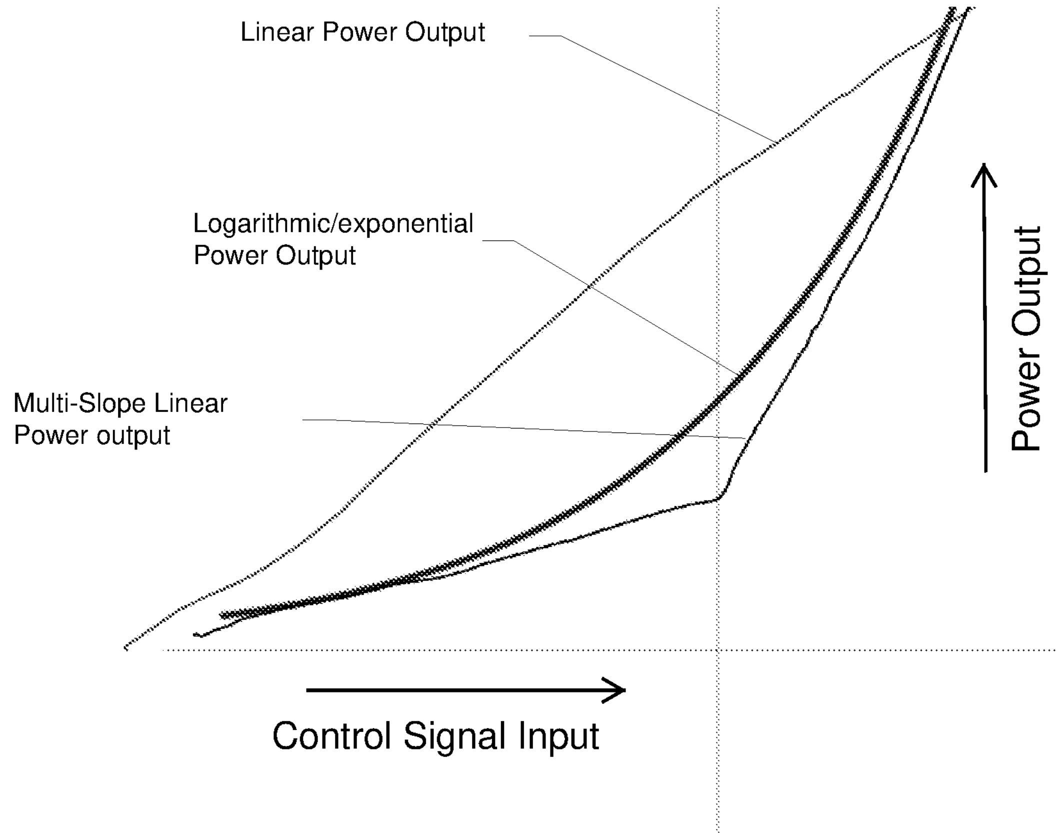
FIG. 11 shows Power Output as a function of Control Signal Input for embodiments of linear, logarithmic or exponential and multi-slope linear algorithms.

Embodiments of a module that maintains or changes the response of the illumination source to the control position or input signal can include, for example, responses that are: linear (also referred to as “simple”), logarithmic or exponential, and multi-slope linear (such as a piecewise linear fit or a linear spline fit.) In an embodiment of a linear algorithm module, the power output to the illumination source 12 can be linear with regard to the control input. The energy can be varied by varying the voltage and/or current directly with the control input, or by varying the duty cycle of the PWM signal. In an embodiment of a linear algorithm module, the measured illumination output can be linear with control input. In an embodiment of a logarithmic or exponential algorithm module, the power output to the illumination source 12 can be logarithmically or exponentially related to the control input, such as by following Equation 1 (combined with the relationship between measured illumination and power delivered to the illumination source 12) or following Equation 2 to approximate a linear perceived brightness response from the light source to the controls, such as over the entire range of illumination or a portion. In an embodiment of a multi-slope linear algorithm module, the power output to the illumination source 12 can be mapped to a series of line segments approximating the slope of sequential portions of a power vs. control output curve, such as is shown in FIG. 11. In an embodiment, the output of any of these algorithm modules can be in the form of a PWM signal, or a signal where the power is a function of the current, a function of the voltage or a function of a combination of current and voltage signal, and a handle or instrument head can select among these forms of the output signal for compatibility with the handle and head being connected to one another.

In an embodiment, for a handle that already produces a PWM output, the PWM output can be modified (if necessary) to produce a PWM signal with an output energy that produces a linear perceived brightness response from the light source to the controls for the light source 12 present in the head. In another embodiment for a handle that already produces a PWM output, a processor, microprocessor or control circuit can convert the PWM signal to a signal where the power is a function of the current, a function of the voltage or a function of a combination of current and voltage signal for compatibility with the handle and head being connected to one another.

Figure 12:
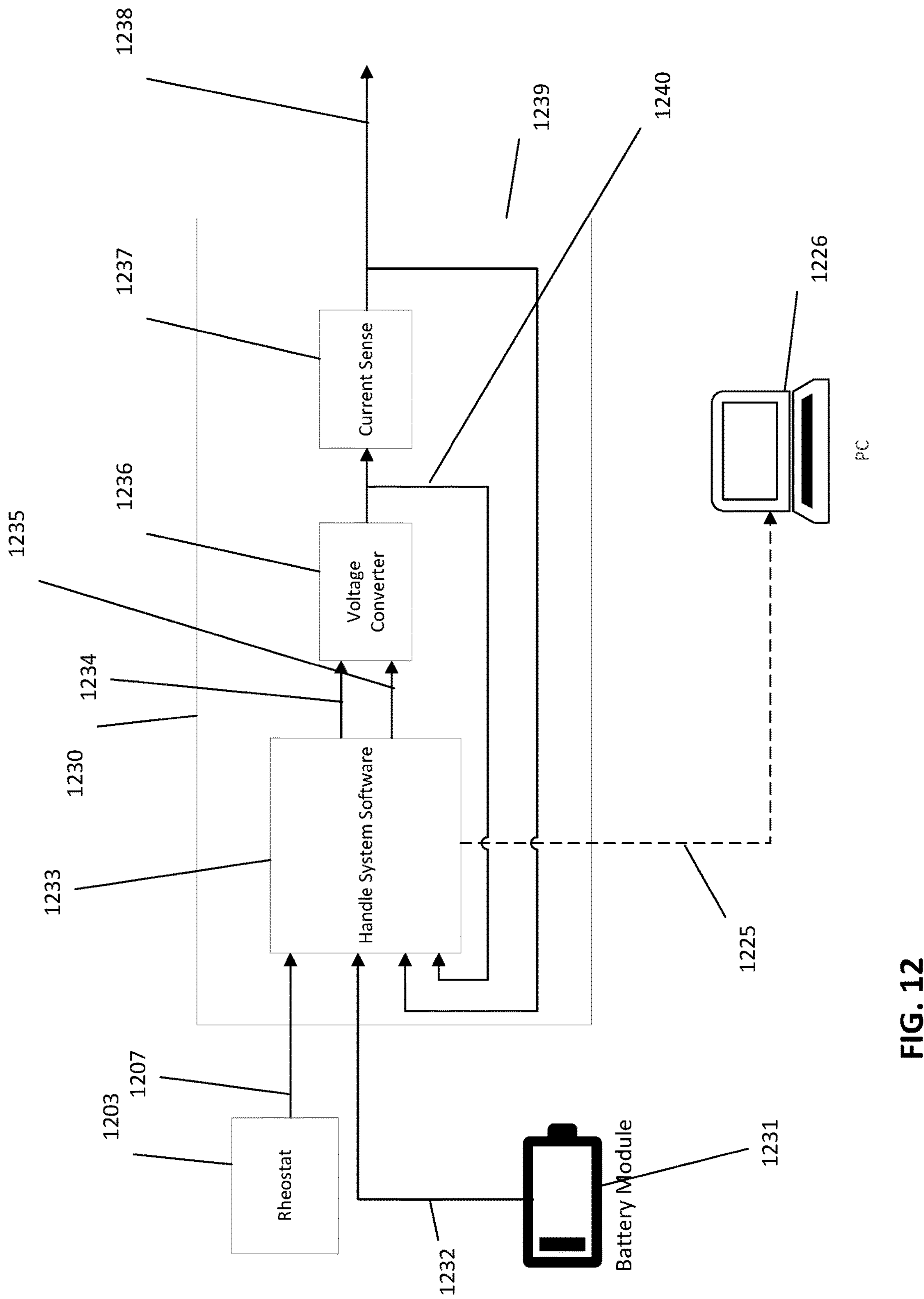
FIG. 12 schematically illustrates an example of an electrical control board for a handle of a medical examination or diagnostic instrument.

FIG. 12 schematically illustrates an example of an electrical control board 1230 for handles 14. In this embodiment, a battery module 1231 directs a battery module power signal (e.g. V) 1232 an handle system software 1233. The handle system software 1233 also receives a control signal, such as a rheostat signal, (e.g. V) 1207 from a rheostat 1203 or other suitable control switch. The handle system software 1233 can send an I2C serial communication signal 1234 and an output enable signal 1235 to a voltage converter 1236, which sends a output signal to a current sensor 1237 (with, for example 0.1 ohm resistance), with a power or voltage out signal 1238. Also included in FIG. 12 is a reference current signal (e.g. V) 1240 and a sensed current signal (e.g. V) 1239 directed to the handle system software 1233. Also shown in FIG. 12 is a port 1225 for debugging, maintenance, programming, etc. which can be used, for example for universal asynchronous receiver/transmitter communications with an external device 1226, such as a computer, a laptop, a phone, or other communications or equipment diagnostic or maintenance device.

While the present disclosure has been primarily described with respect to a light source comprising LEDs, it is to be understood that the techniques described herein may be used with medical examination or diagnostic instruments that include other types of light sources.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

Unless explicitly excluded, the use of the singular to describe a component, structure, or operation does not exclude the use of plural such components, structures, or operations or their equivalents. As used herein, the word “or” refers to any possible permutation of a set of items. For example, the phrase “A, B, or C” refers to at least one of A, B, C, or any combination thereof, such as any of: A; B; C; A and B; A and C; B and C; A, B, and C; or multiple of any item such as A and A; B, B, and C; A, A, B, C, and C; etc.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated. While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof. Use of language such as “approximately”, “somewhat”, “about”, “nearly” and other terms of degree that appear within this disclosure are intended to be interpreted as a person of skill in the art would understand the language based upon the context, with a further understanding that if the context provides insufficient guidance, a tolerance of 20% should be applied. Ranges are inclusive unless the immediate context indicates otherwise.

What is claimed is:

1. A method comprising:

coupling an instrument head to a handle to form a medical diagnostic instrument;

detecting, by the instrument head, a characteristic of the handle;

based at least in part on detecting the characteristic of the handle, determining, by the instrument head, a handle type associated with the handle;

receiving, by the instrument head, an electrical signal from the handle, a magnitude of the electrical signal corresponding to a user input signal;

based at least in part on the handle type, generating a modulated electrical signal by modifying, by the instrument head, the magnitude of the electrical signal; and causing illumination of a light source by supplying, by the instrument head, the modulated electrical signal to the light source, a brightness of the illumination of the light source having a linear relationship with the user input signal, wherein:

the brightness of the illumination of the light source is adjustable over a light output range from a minimum light output to a maximum light output and the user input signal is adjustable over an input signal range from a minimum input signal to a maximum input signal, the brightness of the illumination of the light source is configured to be incremented within the light output range in response to an incremental adjustment of the user input signal to provide an adjusted brightness of the illumination, a ratio of the adjusted brightness of the illumination to the incremental adjustment of the user input signal is approximately a constant over the light output range, and the brightness of the illumination of the light source is stable over the light output range, with not more than about 10% modulation of the brightness of the illumination of the light source at a frequency range of 3-65 Hz.

2. The method of claim 1, wherein the characteristic comprises a polarity of the handle.

3. The method of claim 1, wherein the characteristic comprises:

a second derivative of the magnitude of the electrical signal with respect to time; or a stability of the electrical signal.

4. The method of claim 1, wherein the light source comprises a light-emitting diode (LED) or an incandescent light source.

5. The method of claim 1, wherein the medical diagnostic instrument comprises at least one of an ophthalmoscope or an otoscope.

6. The method of claim 1 further comprising:

detecting, by a processor disposed in the handle, a characteristic of the instrument head; and based at least in part on detecting the characteristic of the instrument head, determining by the processor disposed in the handle, an instrument head type associated with the instrument head.

7. The method of claim 1, wherein the modulated electrical signal comprises a linear, logarithmic or multi-slope linear relationship with respect to the electrical signal.

8. The method of claim 1, wherein generating the modulated electrical signal by modifying, by the instrument head, the magnitude of the electrical signal comprises performing pulse width modulation on the electrical signal.

9. The method of claim 1, further comprising:

generating, by the handle, the electrical signal based on a position of a user input control, wherein the brightness of the illumination of the light source is proportional to the position of the user input control.

10. The method of claim 9, further comprising:

based on an adjustment of the position of the user input control, adjusting, by the handle, the electrical signal;

in response to the handle adjusting the electrical signal, adjusting, by the instrument head, the modulated electrical signal; and in response to the instrument head adjusting the modulated electrical signal, adjusting the brightness of the illumination of the light source by supplying, by the instrument head, the modulated electrical signal to the light source.

11. The method of claim 1, wherein the modulated electrical signal has a logarithmic relationship with respect to the electrical signal from the handle.

12. The method of claim 1, wherein the modulated electrical signal has an exponential relationship with respect to the electrical signal from the handle.

13. The method of claim 1, wherein the modulated electrical signal has a multi-slope linear relationship with respect to the electrical signal from the handle.

14. The method of claim 1, wherein the brightness of the illumination is related to the user input signal according to:

$$\frac{b}{b_{max}} = \sqrt{\frac{u}{u_{max}}},$$

wherein b is the brightness of the illumination, $b_{max}$ is the maximum light output, u is the user input signal, and $u_{max}$ is the maximum input signal.

15. A medical diagnostic instrument comprising:

a handle; and an instrument head comprising:

a light source;

one or more processors; and one or more non-transitory computer-readable media storing computer-executable instructions that, when executed by the one or more processors, cause the one or more processors to perform actions comprising:

detecting a characteristic of the handle;

based at least in part on detecting the characteristic of the handle, determining a handle type associated with the handle;

receiving an electrical signal from the handle, a magnitude of the electrical signal corresponding to a user input signal;

based at least in part on the handle type, generating a modulated electrical signal by modifying the magnitude of the electrical signal; and causing illumination of the light source by supplying the modulated electrical signal to the light source, a brightness of the illumination of the light source having a linear relationship with the user input signal, wherein:

the brightness of the illumination of the light source is adjustable over a light output range from a minimum light output to a maximum light output and the user input signal is adjustable over an input signal range from a minimum input signal to a maximum input signal, the brightness of the illumination of the light source is configured to be incremented within the light output range in response to an incremental adjustment of the user input signal to provide an adjusted brightness of the illumination, a ratio of the adjusted brightness of the illumination to the incremental adjustment of the user input signal is approximately a constant over the light output range, and the brightness of the illumination of the light source is stable over the light output range, with not more than about 10% modulation of the brightness of the illumination of the light source at a frequency range of 3-65 Hz.

16. The medical diagnostic instrument of claim 15, wherein the characteristic comprises a polarity of the handle.

17. The medical diagnostic instrument of claim 15, wherein the medical diagnostic instrument comprises at least one of an ophthalmoscope or an otoscope.

18. A medical diagnostic instrument head, the instrument head comprising:

a light source;

a housing configured to be coupled to a handle; and a processor configured to be in electrical communication with the handle when the housing is mechanically affixed to the handle, the processor being configured to:

receive an electrical signal from the handle, a magnitude of the electrical signal corresponding to a user input signal, the user input signal corresponding to a position of a user input control in the handle;

generating a modulated electrical signal by modifying, by the instrument head, the magnitude of the electrical signal, the modulated electrical signal having a non-linear relationship to the user input signal; and causing illumination of the light source by supplying, by the instrument head, the modulated electrical signal to the light source, a brightness of the illumination of the light source having a linear relationship to the user input signal, wherein:

the brightness of the illumination of the light source is adjustable over a light output range from a minimum light output to a maximum light output and the user input signal is adjustable over an input signal range from a minimum input signal to a maximum input signal, the brightness of the illumination of the light source is configured to be incremented within the light output range in response to an incremental adjustment of the user input signal to provide an adjusted brightness of the illumination, and a ratio of the adjusted brightness of the illumination to the incremental adjustment of the user input signal is approximately a constant over the light output range, and the brightness of the illumination of the light source is stable over the light output range, with not more than about 10% modulation of the brightness of the illumination of the light source at a frequency range of 3-65 Hz.

19. The medical diagnostic instrument head of claim 18, wherein the electrical signal comprises a pulse-width modulation (PWM) signal.

* * * * *